United States Patent [19]

Miyasaka et al.

[11] Patent Number: 4,550,070

[45] Date of Patent: Oct. 29, 1985

[54] DIRECT POSITIVE SILVER HALIDE PHOTOGRAPHIC LIGHT-SENSITIVE MATERIALS

[75] Inventors: Tsutomu Miyasaka; Hidetoshi Kobayashi; Isamu Itoh; Shigeo Hirano, all of Kanagawa, Japan

[73] Assignee: Fuji Photo Film Co., Ltd., Kanagawa, Japan

[21] Appl. No.: 604,554

[22] Filed: Apr. 27, 1984

[30] Foreign Application Priority Data

Apr. 28, 1983 [JP] Japan ................................ 58-75400

[51] Int. Cl.$^4$ .............................................. G03C 5/24
[52] U.S. Cl. .................................... 430/202; 430/598; 430/559; 430/562; 430/940; 430/230
[58] Field of Search ............... 430/202, 230, 598, 559, 430/562, 940

[56] References Cited

U.S. PATENT DOCUMENTS

| | | | |
|---|---|---|---|
| 4,080,207 | 3/1978 | Leone et al. | 430/596 |
| 4,243,739 | 1/1981 | Mitune et al. | 430/600 |
| 4,444,874 | 4/1984 | Silverman et al. | 430/598 |
| 4,448,878 | 5/1984 | Yamamuro et al. | 430/600 |

*Primary Examiner*—Won H. Louie

*Attorney, Agent, or Firm*—Sughrue, Mion, Zinn, Macpeak, and Seas

[57] ABSTRACT

Direct positive silver halide photographic light-sensitive materials are described in which at least one layer of light-sensitive silver halide photographic emulsion layers and other hydrophilic colloid layers applied on a base contains a mercapto compound represented by the following general formula (I) or (II) as a nucleating agent:

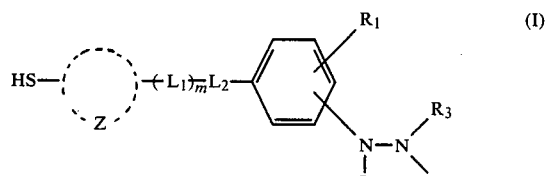

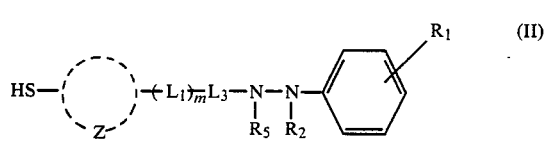

wherein $Z$, $L_1$, $L_2$, $L_3$, $R_1$, $R_2$, $R_3$, $R_4$, $R_5$ and $m$ are as defined in the specification. The nucleating agents can also be added to processing solutions.

9 Claims, No Drawings

DIRECT POSITIVE SILVER HALIDE PHOTOGRAPHIC LIGHT-SENSITIVE MATERIALS

FIELD OF THE INVENTION

The present invention relates to silver halide photographic light-sensitive materials which directly form positive photographic images, and, particularly, the present invention relates to photographic light-sensitive materials containing a novel compound as a nucleating agent (fogging agent) for silver halide.

BACKGROUND OF THE INVENTION

In the field of silver halide photography, a photographic process capable of obtaining positive photographic images without forming negative images or without carrying out intermediate processing is called a direct positive photographic process, and photographic light-sensitive materials and photographic emulsions used for such a photographic process are called direct positive light-sensitive materials and direct positive photographic emulsions, respectively.

Although there are various kinds of direct positive photographic processes, a process which comprises exposing to light previously fogged silver halide grains in the presence of a desensitizer and thereafter developing and a process which comprises exposing to light silver halide emulsions having sensitizing specks in mainly the inner part of silver halide grains and thereafter developing in the presence of a nucleating agent are most available. The present invention relates to the latter process. Silver halide emulsions having sensitizing specks in mainly the inner part of silver halide grains wherein latent images are formed in mainly the inner part of grains are called inner latent image type silver halide emulsions, which are distinguished from silver halide grains wherein latent images are formed mainly on the surface of grains.

The process of directly obtaining positive images by surface development of inner latent image type silver halide photographic emulsions in the presence of a nucleating agent, and photographic emulsions and light-sensitive materials used for such a process are described in, for example, U.S. Pat. Nos. 2,456,953, 2,497,875, 2,497,876, 2,588,982, 2,592,250, 2,675,318, 3,227,552 and 3,317,322, British Pat. Nos. 1,011,062, 1,151,363, 1,269,640 and 2,011,391, Japanese patent publication Nos. 29405/68 and 38164/74, and Japanese patent application (OPI) Nos. 16623/78, 137133/78, 37,732/79, 40629/79, 74536/79, 74729/79, 52055/80 and 90940/80, etc.

In the above described process of directly obtaining positive images, the nucleating agent may be added to a developing solution. However, a better reversal characteristic can be obtained when the nucleating agent is adsorbed on the surface of silver halide grains by adding the nucleating agent to photographic emulsion layers or other suitable layers in the light-sensitive materials.

As nucleating agents used in the above described process of directly obtaining positive images, hydrazines described in U.S. Pat. Nos. 2,563,785 and 2,588,982 and hydrazide and hydrazine compounds described in U.S. Pat. No. 3,227,552 have been known.

However, in the case of using these hydrazine compounds by adding the compounds to emulsion layers, it is necessary to use a considerably high concentration of the compounds (for example, about 2 g per mol of silver). Further, since the nucleating agent moves from the emulsion layers into the developing solution during development processing, the effective amount of the nucleating agent in the emulsions varies causing unevenness of maximum density (nonexposed part), and the nucleating effect in each emulsion layer becomes uneven in the case of multilayer color light-sensitive materials.

Further, it has been known that these nucleating agents generate nitrogen gas during the nucleating reaction. This gas gathers in the film to form bubbles which sometimes cause damage to photographic images.

As nucleating agents which avoid such faults, there are heterocyclic quaternary salt compounds described in U.S. Pat. Nos. 3,615,615, 3,719,494, 3,734,738, 4,094,683 and 4,115,122, British Pat. No. 1,283,835, and Japanese patent application (OPI) Nos. 3426/77 and 69613/77.

However, in silver halide photographic emulsions, sensitizing dyes are added generally for the purpose of spectral sensitization. In particular, in color photographic light-sensitive materials, since these materials require layers sensitive to green light and red light, respectively, in addition to an emulsion layer sensitive to blue light, emulsions for the green-sensitive layer and the red-sensitive layer contain sensitizing dyes for such purposes. When the nucleating agent is present in direct positive emulsions containing a sensitizing dye, competing adsorption of the sensitizing dye and the heterocyclic quaternary salt nucleating agent on silver halide grains occurs, and spectral sensitization is obstructed if the nucleating agent is added in an amount sufficient to form fog nuclei, while formation of fog nuclei is obstructed if the sensitizing dye is added in an amount sufficient to carry out spectral sensitization.

As a method of solving such a difficulty, U.S. Pat. No. 3,718,470 discloses a method using sensitizing dyes also having a nucleating substituent in the molecular structure.

However, in the method of giving a nucleating function and a spectral sensitization function to one molecule, there is a fault that the nucleating function becomes insufficient if used in an amount suitable for spectral sensitization, while the spectral sensitization becomes unsuitable if used in an amount sufficient for the nucleating function.

Further, the hydrazine compounds and the heterocyclic quaternary salt compounds have a common fault that the nucleating function of them has a large temperature dependence. Namely, the nucleating function deteriorates at a lower temperature, while sensitivity reduces at a higher temperature.

In order to solve such problems, it has been suggested to use thiourea attached acylphenylhydrazine compounds described in U.S. Pat. Nos. 4,030,925, 4,031,127, 4,139,387, 4,245,037, 4,255,511 and 4,276,364 and British Pat. No. 2,012,443, etc.

However, compounds described in the above described U.S. Patents are nearly insoluble in water and have very low solubility in organic solvents. Therefore, in order to add the above described compounds to hydrophilic colloid layers such as light-sensitive layers, etc., it is necessary to have a process which comprises dissolving once the above described compounds in a large amount of organic solvents and adding the resulting solution to a hydrophilic colloid solution. However, when a large amount of organic solvent is added to the hydrophilic colloid solution, hydrophilic substances such as gelatin, etc. contained in the solution easily cause separation or aggregation. If such a hydrophilic colloid solution is applied to a base, there is the possibility of causing uneven application and deterioration of the quality of light-sensitive materials because of precipitates or aggregates formed in the colloid layer.

In order to improve various properties of nucleating agents, there are other reports which disclose nucleating agents having a structure wherein various kinds of adsorbing groups are attached to an acylhydrazine skeleton as a nucleating site.

Namely, those using heterocyclic thioamide as an adsorbing group have been described in U.S. Pat. No. 4,080,207, and those using triazole derivatives have described in U.S. Pat. No. 4,278,748. However, because none of these compounds are sufficiently adsorbed on the surface of a silver halide, the amount of the compounds required is comparatively large or the nucleating function of the compounds has a tendency of having great dependence on processing temperature or preservation temperature of sensitive materials. Moreover, phenylacylhydrazine nucleating agents having a mercapto group containing heterocyclic group as an adsorbing group have been described in British Pat. No. 2,011,391B, wherein examples of the adsorbing group include groups of benzotriazole-2-thiols, 1-phenyl-5-mercaptotetrazoles and 1,2,3-benzotriazine-4-thiols. However, these nucleating agents have practical faults in that they not only have comparatively inferior preservation stability but also are difficult to synthesize because of their chemical structure.

SUMMARY OF THE INVENTION

Accordingly, the first object of the present invention is to provide direct positive photographic light-sensitive materials capable of directly forming positive images having uniform high maximum density.

The second object of the present invention is to provide direct positive photographic light-sensitive materials containing a nucleating agent which gives the desired nucleating function in a small amount without obstructing spectral sensitization.

The third object of the present invention is to provide direct positive photographic light-sensitive materials having small dependence on developing temperature.

The fourth object of the present invention is to provide direct positive photographic light-sensitive materials containing a nucleating agent which is easily synthesized and has excellent preservation stability.

The fifth object of the present invention is to provide direct positive photographic light-sensitive materials forming direct positive images having good quality.

The sixth object of the present invention is to provide color diffusion transfer photographic light-sensitive materials having the above described characteristics.

These and other objects of the present invention have been attained by incorporating a mercapto compound represented by the general formula (I) or (II) described below as a nucleating agent in at least one hydrophilic colloid layer in silver halide light-sensitive materials, preferably, an inner latent image type silver halide photographic emulsion layer or an adjacent hydrophilic colloid layer. This nucleating agent may also be added to processing solutions.

The nucleating agents of the present invention are distinctly different from those described in the above described British Pat. No. 2,011,391B from the viewpoint of chemical structure as follows. Namely, the nucleating agents described in the British Patent are characterized in that the adsorbing group for silver halide and the acylhydrazine group are connected through at least a group wherein a methine chain is bonded to a phenylene group

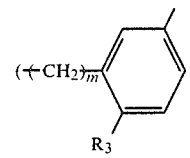

wherein m is an integer of 1 to 4).

In contrast, the nucleating agent of the present invention (general formula (I)) are characterized in that a mercapto group containing heterocyclic group (adsorbing group) and an acylhydrazine group are connected through the group:

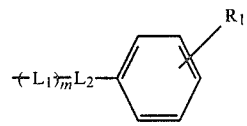

wherein $L_2$ does not contain a methine group, and m is 0 or 1. Accordingly, the nucleating agents of the present invention are distinctly different in chemical structure from the nucleating agents described in the British Patent.

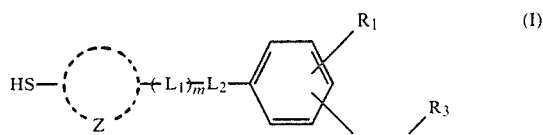

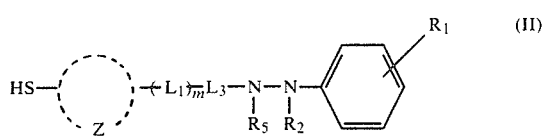

wherein Z represents an atomic group necessary to form a mononuclear or condensed nitrogen-containing heterocyclic ring, $L_1$ represents a divalent organic group, m represents 0 or 1, $L_2$ represents —CONR—, —NRCO—, —SO$_2$NR—, NRSO$_2$—, OCO—, —COO—, —S—, —NR—, —CO—, —SO—, —SO$_2$—, —OCOO—, —NRCONR'—, —NRCOO—, —OCONR— or —NRSO$_2$NR'—, wherein R and R' each represents a hydrogen atom, an alkyl group or an aryl group, $L_3$ represents —CO—, —SO— or —SO$_2$—, $R_1$ represents a hydrogen atom, an alkyl group, a halogen atom, an alkoxy group, a carbonamide group or a sulfonamide group, $R_2$ represents a hydrogen atom or an alkoxycarbonyl group, $R_3$ represents an acyl group, an alkylsulfonyl group, an arylsulfonyl group, an alkylsulfinyl group, an arylsulfinyl group, an alkoxycarbonyl group, an aryloxycarbonyl group, a carbamoyl group, a sulfamoyl group or a sulfinamoyl group, $R_4$ represents a hydrogen atom, and $R_3$ may form the partial structure:

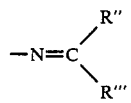

of hydrazone together with $R_4$ and a nitrogen atom, and $R_5$ represents a hydrogen atom or forms the partial structure:

of hydrazone together with $L_3$ and a nitrogen atom, wherein one of two bonds of the carbon atom in

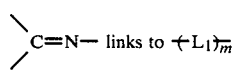

and the other of two bonds of the carbon atom links to R''. R'' represents an alkyl group, an aryl group or a heterocyclic group, and R''' represents a hydrogen atom, an alkyl group, an aryl group or a heterocyclic group.

DETAILED DESCRIPTION OF THE INVENTION

In the general formulas I and II, the heterocycle represented by Z may be substituted with suitable substituents in addition to the mercapto group and $-L_1)_m$, and Z is a 5-membered to 7-membered ring which may form a condensed ring together with another heterocycle or benzene ring. Further, the mercapto group on the heterocycle represented by Z may form, for example, the following thione structure by tautomerism.

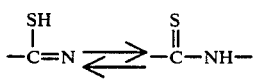

The preferred number of nitrogen atoms composing the heterocycle represented by Z is 1 to 4 in the case of a mononuclear ring and a total of 1 to 6 in the case of a condensed ring.

Examples of preferred heterocycles represented by Z include pyrrole, pyrazole, imidazole, triazole, tetrazole, pyridine, pyrimidine, pyrazine, pyridazine, triazine, imidazole, benzimidazole and azaindene, etc. The divalent organic group represented by $L_1$ is composed of divalent groups such as alkylene, alkenylene, phenylene, —O—, —S—, —CO—, —SO—, —SO$_2$— and imido, etc. (alone or in combination). Examples of $L_1$ include the following.

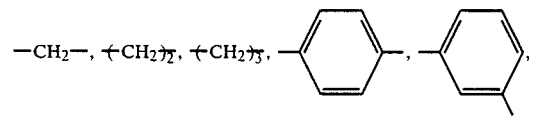

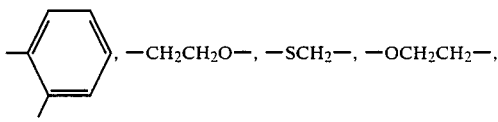

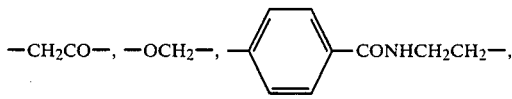

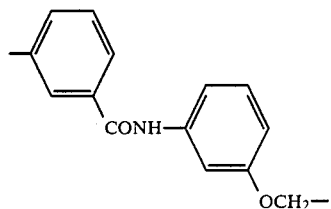

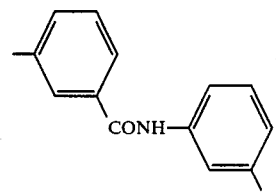

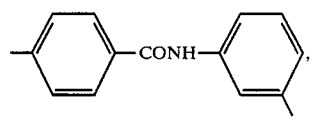

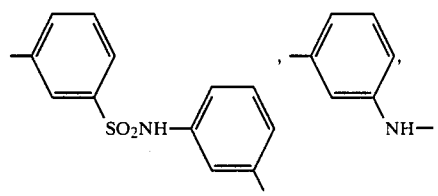

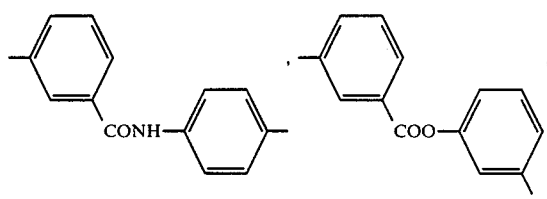

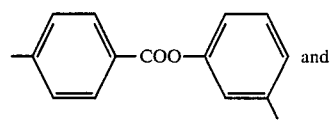

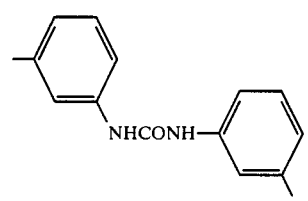

$R_1$ represents a hydrogen atom, an alkyl group (a methyl group, an ethyl group, etc.), a halogen atom (Cl, Br, etc.), an alkoxy group (a methoxy group, a methoxyethoxy group, etc.), a carbonamide group (an acetamide group, etc.) or a sulfonamide group (a methanesulfonamide group, etc.). $R_2$ represents a hydrogen atom or an alkoxycarbonyl group (a methoxycarbonyl group, an ethoxycarbonyl group, etc.). $R_3$ represents an acyl group ( a formyl group, an acetyl group, a propionyl group, a trifluoroacetyl group, a chloroacetyl group, a benzoyl group, a 4-chlorobenzoyl group, a pyruvoyl group, a methoxyalyl group, a methyloxamoyl group, etc.), an alkylsulfonyl group (a methanesulfonyl) group, a 2-chloroethanesulfonyl group, etc.), an arylsulfonyl group (a benzenesulfonyl group, etc.), an alkylsulfinyl group (a methanesulfinyl group, etc.), an arylsulfinyl group (a benzenesulfinyl group, etc.), an alkoxycarbonyl group (a methoxycarbonyl group, a methoxyethoxycarbonyl group, etc.), an aryloxycarbonyl group (a phenoxycarbonyl group, etc.), a carbamoyl group (a methylcarbamoyl group, a phenylcarbamoyl group, etc.), a sulfamoyl group (a dimethylsulfamoyl group, etc.) or a sulfinamoyl group (a methylsulfinamoyl group, etc.). Examples of hydrazones formed by $R_3$ and $R_4$ include acetonehydrazone, benzaldehyde hydrazone, o-hydroxybenzaldehyde hydrazone, etc.

Groups represented by $R_1$ to $R_4$ should not be interpreted to be limited to the above exemplified groups, but they include, for example, groups having suitable substituents.

Of compounds represented by the general formulas (I) and (II), particularly preferred compounds are those represented by the following general formula (III).

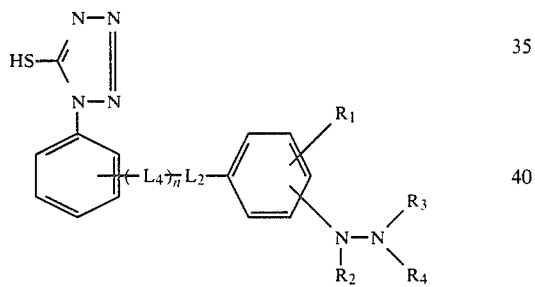

wherein $L_2$, $R_1$, $R_2$, $R_3$ and $R_4$ have the same meaning as in the general formula (I), n represents 0 or 1, and $L_4$ is selected from $L_1$ in the general formula (I).

Examples of compounds used as available nucleating agents in the present invention are as follows.

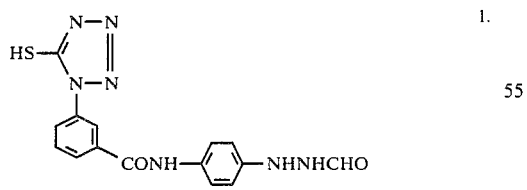

1.

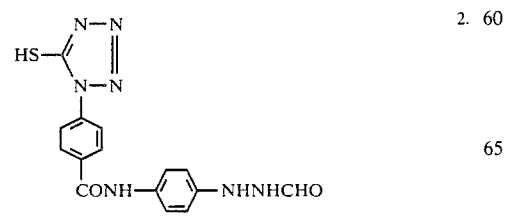

2.

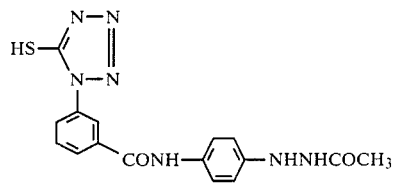

3.

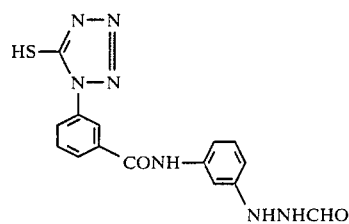

4.

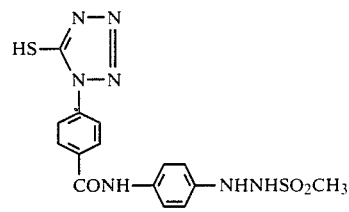

5.

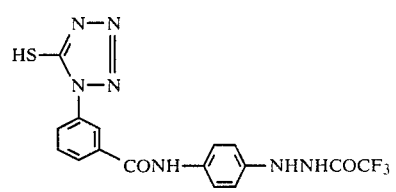

6.

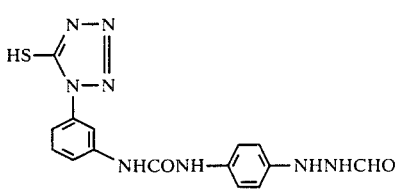

7.

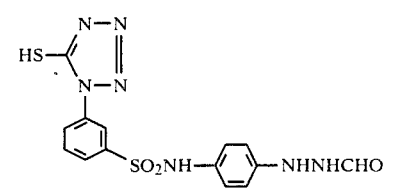

8.

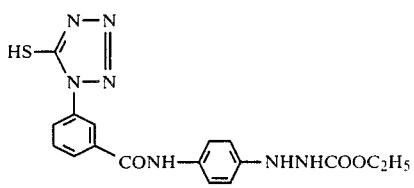

9.

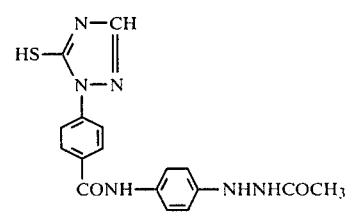

10.

-continued
11. 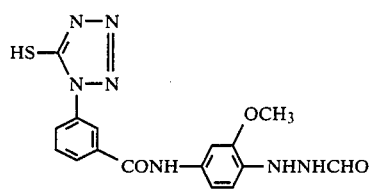
12. 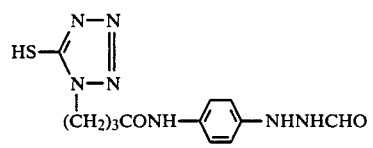
13. 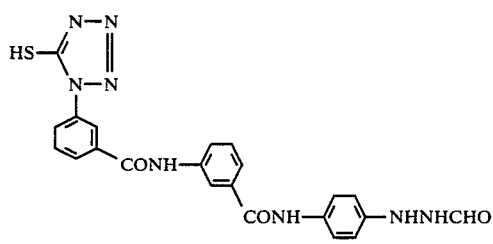
14. 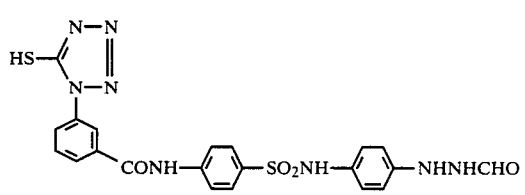
15. 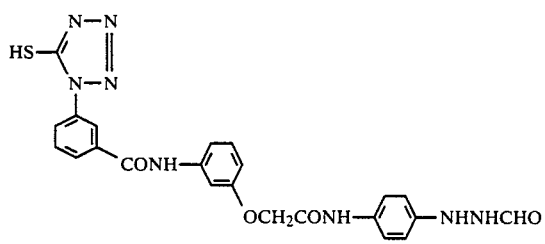
16. 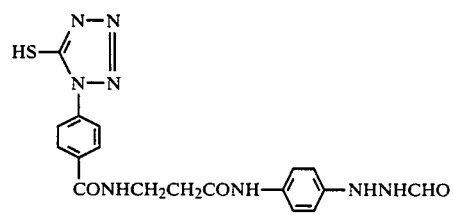
17. 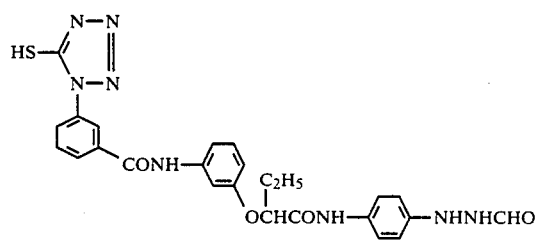
-continued
18. 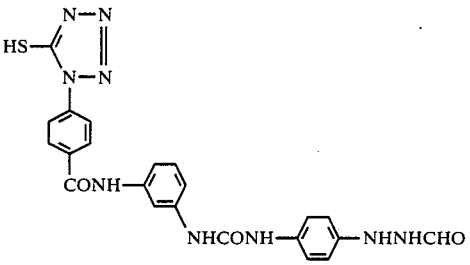
19. 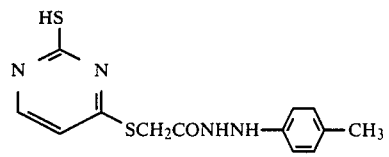
20. 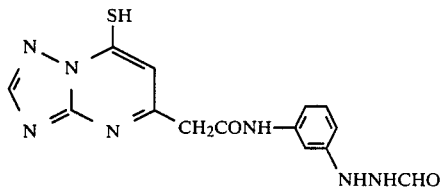
21. 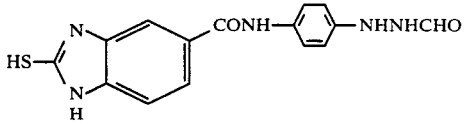
22. 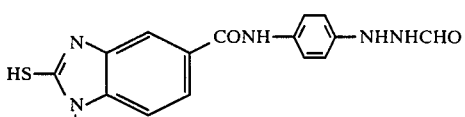
23. 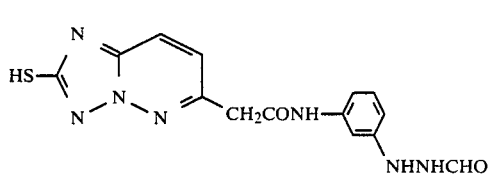
24. 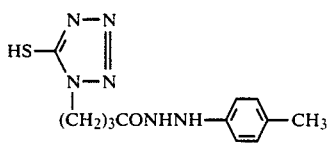
25. 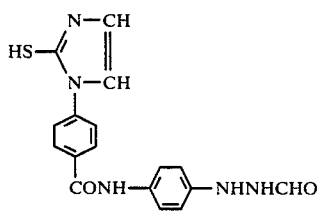
26. 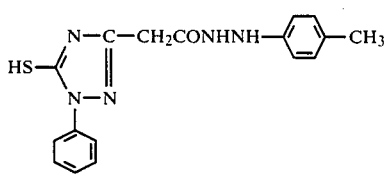

-continued

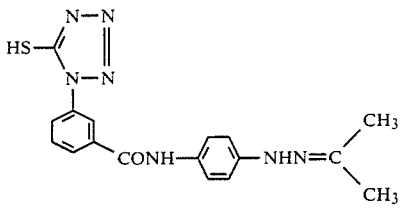

27.

Examples of synthesis of the compounds of the present invention are described in the following Examples.

SYNTHESIS EXAMPLE 1

Synthesis of Compound 1

82.5 g of ethyl m-aminobenzoate was dissolved in 500 ml of toluene. To the resulting solution, 83.4 g of N,N-diethylthiocarbamoyl chloride was added dropwise over about 1 hour with stirring at room temperature, and the mixture was refluxed for 5 hours with heating. Toluene was distilled away under a reduced pressure. 300 ml of ethyl acetate was added, and the ethyl acetate solution was washed with water. After ethyl acetate was distilled away under a reduced pressure, 80 g of oily ethyl m-isothiocyanate-benzoate was obtained by further distillation under a reduced pressure. Boiling point: 125° C./0.6 mm Hg. Yield: 77%

500 ml of water was added to a mixture of 69 g of ethyl m-isothiocyanate-benzoate and 26 g of sodium azide and the mixture was refluxed for 2 hours with heating. After the precipitated insoluble substances were filtered out, concentrated hydrochloric acid was added to the filtrate to acidify the filtrate (pH: 2). Precipitated crystals of 1-(3-ethoxycarbonylphenyl)-5-mercaptotetrazole were filtered off. After 30 g of sodium hydroxide and 300 ml of water were added, the mixture was heated to 70° C. and stirred for 30 minutes. The reaction solution was neutralized with concentrated hydrochloric acid, and the precipitated crystals were filtered out. Crude crystals were recrystallized from methanol to obtain 32 g of 1-(3-carboxyphenyl)-5-mercaptotetrazole. Yield: 42%. Melting point: 181°–182° C.

Then, 1-formyl-2-(4-aminophenyl)hydrazine was synthesized according to the process described in Japanese Patent Application (OPI) 74729/79. Namely, to 1.6 l of acetonitrile, 459 g of 4-nitrophenylhydrazine was added and thereafter 322 g of formic acid was added slowly with stirring to prepare a uniform solution. After 20 minutes, crystals were precipitated. After the reaction was carried out at 80° C. for 2 hours, the reaction solution was cooled and crystals were filtered off, washed with acetonitrile and dried to obtain 495 g of 1-formyl-2-(4-nitrophenyl)-hydrazine. Melting point: 184°–186° C.

Then, 30 g of 1-formyl-2-(4-nitrophenyl)hydrazine was catalytically reduced at room temperature in 1.6 l of ethanol using palladium-carbon catalyst. The filtrate was evaporated to dryness, by which 20.5 g of light brown solid of 1-formyl-2-(4-aminophenyl)hydrazine was obtained. Melting pont: 123°–125° C.

11.1 g of 1-(3-carboxyphenyl)-5-mercaptotetrazole and 7.6 g of 1-formyl-2-(4-aminophenyl)hydrazine were dissolved in 50 ml of dimethylformamide. To the resulting solution, a solution prepared by dissolving 10.3 g of dicyclocarbodiimide in 5 ml of dimethylformamide was added dropwise over 15 minutes with stirring at 0° C. under a nitrogen atmosphere. After conclusion of the addition, the mixture was stirred for 1 hour and thereafter it was further stirred at 25° C. for 2 hours. The formed dicyclohexylurea was removed by filtration, and 1.5 l of iced water was added to the filtrate. The precipitated crude crystals were filtered off and they were dispersed in 100 ml of methanol with heating for 15 minutes. After being cooled to room temperature, the dispersion was filtered to obtain 9.6 g of the desired Compound 1. Yield: 54%. Melting point: 198°–200° C.

| Elemental analysis $C_{15}H_{13}N_7O_2S$ | | | |
|---|---|---|---|
| Element | H % | C % | N % |
| Calculated value | 3.69 | 50.70 | 27.59 |
| Found value | 3.74 | 50.45 | 27.54 |

SYNTHESIS EXAMPLE 2

Synthesis of Compound 2

82.5 g of ethyl p-aminobenzoate was dissolved in 500 ml of toluene. After 83.4 g of N,N-diethylthiocarbamoyl chloride was added, the mixture was refluxed for 8 hours with heating. After being cooled with iced water, 100 ml of concentrated hydrochloric acid was added, and the toluene layer was washed with water. After toluene was distilled away under a reduced pressure, the oily product was crystallized from methanol to obtain 77.1 g of ethyl p-isothiocyanate-benzoate. Yield: 74.5%. Melting point: 52° C.

31 g of ethyl p-isothiocyanate-benzoate and 11.7 g of sodium azide was dispersed in 300 ml of water, and the dispersion was refluxed for 5 hours with heating. After being cooled to room temperature, concentrated hydrochloric acid was added to acidify (pH: 2). Precipitated crystals of 1-(4-ethoxycarbonylphenyl)-5-mercaptotetrazole were filtered off. After 25 g of sodium hydroxide and 500 ml of water were added, the mixture was stirred at 70° C. for 30 minutes. After being cooled to room temperature, concentrated hydrochloric acid was added to neutralize and precipitated crystals were filtered off. By carrying out recrystallization from methanol, 40 g of 1-(4-carboxyphenyl)-5-mercaptotetrazole was obtained. Yield: 48%. Melting point: 198° C.

Using 11.1 g of 1-(4-carboxyphenyl)-5-mercaptotetrazole and 7.6 g of 1-formyl-2-(4-aminophenyl)hydrazine, 8.0 g of the desired Compound 2 was obtained by the same manner as in Synthesis Example 1. Yield: 45%. Melting point: 190°–196° C.

| Elemental analysis $C_{15}H_{13}N_7O_2S$ | | | |
|---|---|---|---|
| Element | H % | C % | N % |
| Calculated value | 3.69 | 50.70 | 27.59 |
| Found value | 3.78 | 50.48 | 27.52 |

SYNTHESIS EXAMPLE 3

Synthesis of Compound 3

15.3 g of p-nitrophenylhydrazine and 10.1 g of triethylamine were dissolved in 100 ml of acetonitrile, and 7.9 g of acetyl chloride was added dropwise over 15 minutes with cooling with water. After conclusion of the addition, the mixture was stirred at 25° C. for 1 hour and thereafter 100 ml of water as added thereto. The precipitated crystals were filtered off, and washed with acetonitrile to obtain 16.6 g of 1-acetyl-2-(4-nitrophenyl)hydrazine. Yield: 16.6 g. Melting point: 209°–214° C.

16.6 g of 1-acetyl-2-(4-nitrophenyl)hydrazine was catalytically reduced at room temperature in 800 ml of ethanol using a palladium-carbon catalyst. The reaction solution was filtered and cooled to obtain 10.5 g of 1-acetyl-2-(4-aminophenyl)hydrazine. Yield: 75%. Melting point: 130°–140° C.

4.4 g of 1-(3-carboxyphenyl)-5-mercaptotetrazole and 3.3 g of 1-acetyl-2-(4-aminophenyl)hydrazine were dissolved in 20 ml of dimethylformamide. To the resulting solution, a solution prepared by dissolving 4.1 g of dicyclohexylcarbodiimide in 5 ml of dimethylformamide was added dropwise over 15 minutes with stirring at 0° C. under a nitrogen atmosphere. After addition, the mixture was stirred for 2 hours and it was then further stirred at 24° C. for 4 hours. The formed dicyclohexylurea was removed by filtration, and 1 l of iced water was added to the filtrate. Crude crystals were filtered off and purified by a chromato-column packed with silica gel using chloroformethanol as a developer to obtain 3.5 g of the desired Compound 3. Yield: 48%. Melting point: 178°–182° C.

| Elemental analysis $C_{16}H_{15}N_7O_2S$ | | | |
|---|---|---|---|
| Element | H % | C % | N % |
| Calculated value | 4.09 | 52.02 | 26.54 |
| Found value | 4.12 | 51.85 | 26.51 |

SYNTHESIS EXAMPLE 4

Synthesis of Compound 13

68.2 g of 1-formyl-2-(4-aminophenyl)hydrazine and 60 ml of triethylamine were dissolved in 500 ml of acetonitrile. To the resulting solution, 70 g of 3-nitrobenzoyl chloride was added dropwise with stirring while keeping the solution temperature at less than 50° C., by which crystals precipitated. After being heated to 60° C. for a further 2 hours, it was cooled and poured into water. Crystals were filtered off and recrystallized from ethanol to obtain 72.8 g of 1-formyl-2-(4-(3-nitrobenzamido)phenyl)hydrazine. Yield: 54%. Melting point: 185°–187° C.

800 ml of isopropanol, 80 ml of water, a small amount of ammonium chloride and 12 g of 1-formyl-2-(4-(3-nitrobenzamide)phenyl)hydrazide were blended, and the mixture was stirred with heating on a steam bath. To the mixture, 80 g of iron powder was added and it was refluxed for 1 hour. The reaction solution was filtered and the filtrate was concentrated to about 200 ml under a reduced pressure, and cooled to room temperature. Precipitated crystals were filtered off to obtain 8.0 g of 1-formyl-2-(4-(3-aminobenzamide)phenyl)hydrazine. Yield: 74%. Melting point: 177°–178° C.

Using 4.4 g of 1-(3-carboxyphenyl)-5-mercaptotetrazole and 5.4 g of 1-formyl-2-(4-(3-aminobenzamide)phenyl)hydrazine, 5.3 g of the desired Compound 13 was obtained by the same manner as in Synthesis Example 1. Yield: 56%. Melting point: 168°–174° C.

| Elemental analysis $C_{22}H_{18}N_8O_3S$ | | | |
|---|---|---|---|
| Element | H % | C % | N % |
| Calculated value | 3.82 | 55.69 | 23.62 |
| Found value | 3.95 | 55.57 | 23.54 |

SYNTHESIS EXAMPLE 5

Synthesis of Compound 24

13 g of ethyl 4-aminobutanoate was dissolved in 100 ml of chloroform. To the resulting solution, 20.2 g of triethylamine and 7.6 g of carbon disulfide and 10.8 g of ethyl chlorocarbonate were added dropwise in turn with stirring at 0° C. After conclusion of the addition, the mixture was stirred at room temperature for 1 hour and then at 50° C. for another 1 hour. After the reaction solution was washed with water, chloroform was distilled away. To the residue, 10 g of sodium azide and 100 ml of water were added, and the mixture was refluxed for 5 hours with heating while vigorously stirring. After cooling to room temperature, 16.8 g of potassium hydroxide was added and the mixture was stirred for 1 hour. To the reaction solution, hydrochloric acid was added to acidify the solution. Precipitated crystals were filtered off to obtain 13.9 g of 1-(3-carboxypropyl)-5-mercaptotetrazole. Yield: 74%. Melting point: 90°–95° C.

9.4 g of 1-(3-carboxypropyl)-5-mercaptotetrazole and 6.1 g of p-tolylhydrazine were dissolved in 50 ml of dimethylformamide. To the resulting solution, a solution prepared by dissolving 10.3 g of dicyclohexylcarbodiimide in 20 ml of formamide was added dropwise over 30 minutes with stirring at 0° C. under a nitrogen atmosphere. After stirring at room temperature for 5 hours, the reaction solution was added to 1 l of iced water. Precipitated crude crystals were filtered off and recrystallized from methanol to obtain 6.4 g of the desired Compound 24. Yield: 44%. Melting point: 112°–114° C.

| Elemental analysis | | | |
|---|---|---|---|
| Element | H % | C % | N % |
| Calculated value | 5.52 | 49.30 | 28.75 |
| Found value | 5.56 | 49.14 | 28.66 |

Compounds of the present invention can be synthesized by various processes. For example, in the case that $L_2$ in the general formula (I) is —CONH—, the following process can be used:

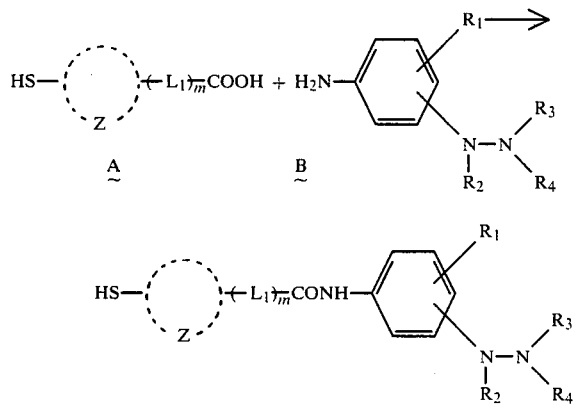

In the case that $L_3$ in the general formula (II) is CO, the following process can be used:

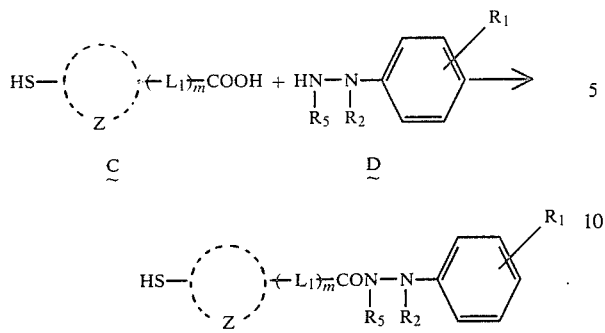

In these reactions, condensation can be carried out in a solvent such as acetonitrile, tetrahydrofuran, dioxane, methylene chloride, chloroform, dimethylformamide, dimethylacetamide, etc. using a condensing agent such as dicyclohexylcarbodiimide, carbonyldiimidazole, etc. In these cases, it is possible to use catalysts such as N,N-dimethylaminopyridine, pyrrolidinopyridine, N-hydroxybenzotriazole, etc. or bases such as triethylamine, N-ethylpiperidine, N-ethylmorpholine, pyridine, etc. for the purpose of improving yield or shortening reaction time.

In addition to these reactions, it is possible to obtain the desired products by converting the above compound A or C into a mixed acid anhydride with chloroformic acid esters such as ethyl chloroformate, isobutyl chloroformate, etc. in a solvent such as dimethylformamide, dimethylacetamide, etc. in the presence of a base such as pyridine, triethylamine, etc. and carrying out a condensation reaction with the aniline compound B or the hydrazine compound D, respectively. The process for synthesizing the aniline compounds B have been described in Japanese Patent Application (OPI) 74729/79.

In direct positive light-sensitive materials of the present invention, compounds represented by the general formulas (I) and (II) are preferred to be incorporated in an inner latent image type silver halide emulsion layer, but they may be incorporated in a hydrophilic colloid layer adjacent to the inner latent image type silver halide emulsion layer. Such a layer may be any layer if the function of the layer does not prevent diffusion of the nucleating agent into silver halide grains, such as a coloring matter layer, an intermediate layer, a filter layer, a protective layer, an antihalation layer, etc.

It is preferred that the content of the nucleating agent of the present invention in the layer is such an amount that a sufficient maximum density (for example, 1.0 or more as silver density) is obtained when the inner latent image type emulsion is developed with a surface developing solution. Practically, since the content varies according to the characteristics of the silver halide used, the chemical structure of the nucleating agent, and the developing conditions, a suitable content can vary in a wide range, but it is practically available in a range of about 0.005 mg to 500 mg and preferably in the range of about 0.01 mg to about 100 mg per mol of silver in the inner latent image type silver halide emulsion. In the case that the nucleating agent is incorporated in a hydrophilic colloid layer adjacent to the emulsion layer, it is incorporated in the same amount as that based on silver content contained in the same area of the inner latent image type emulsion layer. The inner latent image type silver halide emulsion can be clearly defined by the fact that a maximum density attained in the case of developing with an "inner type" developing solution after exposure is larger than that attained in case of developing with a "surface type" developing solution. The inner latent image type emulsions suitable for the present invention are those wherein a maximum density measured by a conventional method of measuring photographic densities which is obtained in the case of exposing to light the silver halide emulsion applied to a transparent base for a fixed time in a range of 0.01 to 1 second and developing with the following developing solution (inner type developing solution) at 20° C. for 3 minutes is at least 5 times higher than a maximum density which is obtained in the case of developing the silver halide emulsion exposed to light by the same manner as described above with the following developing solution B (surface developing solution) at 20° C. for 4 minutes.

| Developing Solution A | |
|---|---|
| Hydroquinone | 15 g |
| Monomethyl-p-aminophenol sesquisulfate | 15 g |
| Sodium sulfite | 50 g |
| Potassium bromide | 10 g |
| Sodium hydroxide | 25 g |
| Sodium thoosulfate | 20 g |
| Water | to make 1 l |
| Developing Solution B | |
| p-Oxyphenylglycine | 10 g |
| Sodium carbonate | 100 g |
| Water | to make 1 l |

The inner latent image type silver halide emulsions used in the present invention are hydrophilic colloid dispersions of silver chloride, silver bromide, silver chlorobromide, silver iodobromide, silver chloroiodobromide or a mixture thereof. Composition of halides is selected according to the purpose of use or processing conditions, but it is particularly preferred to use silver bromide, silver iodobromide or silver chloroiodobromide which has an iodide content of 10% by mol or less and a chloride content of 30% by mol or less. As suitable emulsions, there are not only emulsions described in the above U.S. Pat. No. 2,592,250 but also conversion type emulsions, core/shell type emulsions, emulsions doped with other metals, etc. described in British Pat. No. 1,027,146 and U.S. Pat. Nos. 3,206,313, 3,511,662, 3,447,927, 3,737,313, 3,761,276 and 3,935,014, etc. However, the present invention is not limited to these emulsions.

In light-sensitive materials of the present invention, various kinds of photographic bases can be used. Silver halide emulsions may be applied to one side or both sides of the base.

In the light-sensitive materials of the present invention, other additives and, particularly, additives available for photographic emulsions, for example, lubricants, stabilizers, hardeners, sensitizing agents, light absorbing dyes and plasticizers, etc. can be added to silver halide emulsion layers and other hydrophilic colloid layers.

Further, in the present invention, the silver halide emulsions may contain compounds which release iodine ions (for example, potassium iodide, etc.). Further, it is possible to obtain desired images with a developing solution containing iodine ions.

In light-sensitive materials of the present invention, photographic emulsions may be spectrally sensitized to blue light having comparatively long wavelengths, green light, red light or infrared light with sensitizing dyes. As sensitizing dyes, it is possible to use cyanine dyes, merocyanine dyes, complex cyanine dyes, complex merocyanine dyes, polar cyanine dyes, styryl dyes, hemicyanine dyes, oxonol dyes, hemioxonol dyes, etc. These sensitizing dyes include cyanine dyes and merocyanine dyes described in U.S. patent application Ser. Nos. 527,922 (Aug. 30, 1983), 528,010 (Aug. 31, 1983) and 526,926 (Aug. 26, 1983).

The sensitizing dyes used in the present invention are used in the same amount as that used for conventional negative silver halide emulsions. It is particularly advantageous to use them in such an amount that they do not substantially reduce the intrinsic sensitivity of silver halide emulsions. The sensitizing dyes are preferred to be used in an amount of about $1.0 \times 10^{-5}$ to about $5 \times 10^{-4}$ mols per mol of silver halide and, preferably, $4 \times 10^{-5}$ to $2 \times 10^{-4}$ mols per mol of silver halide.

In the light-sensitive materials of the present invention, it is possible to incorporate color image forming couplers as coloring matters. Alternatively, it is possible to develop them with a developing solution containing color image forming couplers.

In the present invention, developing agents such as hydroxybenzenes (for example, hydroquinones), aminophenols or 3-pyrazolidones, etc. may be incorporated in emulsions or light-sensitive materials.

The photographic emulsions used in the present invention can be combined with dye image donative compounds (coloring matters) for color diffusion transfer processes which release a diffusible dye corresponding to development of silver halide, by which it is possible to obtain desired transfer images of an image receiving layer after carrying out suitable development processing. As such coloring matters for color diffusion transfer process, several substances have been known. For example, it is possible to use compounds described in U.S. Pat. Nos. 3,227,551, 3,227,554, 3,443,939, 3,443,940, 3,443,930, 3,443,943, 3,628,952, 3,844,785, 3,658,524, 3,698,897, 3,725,062, 3,728,113, 3,751,406, 3,929,760, 3,931,144, 3,932,381, 3,928,312, 4,013,633, 3,932,380, 3,954,476, 3,942,987, 4,013,635, 4,053,312, 4,055,428, 4,268,625 and 4,336,322, U.S. patent Publication (USB) 351,673, British Pat. Nos. 840,731, 904,364 and 1,038,331, German Patent Application (OLS) 1,930,215, 2,214,381, 2,228,361, 2,317,134 and 2,402,900, French Pat. No. 2,284,140, Japanese patent applications (OPI) Nos. 46730/78, 130122/79, 16130/81, 650/82, 4043/82 and 104343/76, and Japanese patent application (OPI) No. 12642/81 and Japanese Publication No. 48894/83, etc. Among others, it is preferred to use coloring matters which are originally nondiffusible but are cleaved by an oxidation-reduction reaction with an oxidation product of the developing agent (or electron transfer agent) to release a diffusible dye (hereinafter, referred to as DRR compounds). Particularly, it is preferred to use DRR compounds having a N-substituted sulfamoyl group. Preferred compounds used together with the nucleating agents of the present invention are, particularly, DRR compounds having an o-hydroxyarylsulfamoyl group described in the above described U.S. Pat. Nos. 4,005,428, 4,053,312 and 4,336,322, etc. and DRR compounds having a redox nucleus described in U.S. Pat. No. 4,268,625. When the nucleating agents are used together with such DRR compounds, temperature dependence in case of, particularly, carrying out processing becomes remarkably small.

Examples of DRR compounds include 1-hydroxy-2-tetramethylenesulfamoyl-4-(3'-methyl-4'-(2"-hydroxy-4"-methyl-5"-hexadecyloxyphenylsulfamoyl)-phenylazo)naphthalene as a magenta dye forming substance and 1-phenyl-3-cyano-4-(3'-(2"-hydroxy-4"-methyl-5"-(2''',4'''-di-tert-pentylphenoxyacetamino)-phenylsulfamoyl)phenylazo)-5-pyrazolone as a yellow dye image forming substance in addition to those described in the above described patent specifications.

In order to develop the light-sensitive materials of the present invention, various known developing agents can be used. Namely, it is possible to use polyhydroxybenzenes, for example, hydroquinone, 2-chlorohydroquinone, 2-methylhydroquinone, catechol and pyrogallol, etc.; aminophenols, for example, p-aminophenol, N-methyl-p-aminophenol, N-methyl-p-aminophenol and 2,4-diaminophenol, etc.; 3-pyrazolidones, for example, 1-phenyl-3-pyrazolidone, 4,4-dimethyl-1-phenyl-3-pyrazolidone, 4,4-dihydroxymethyl-1-phenyl-3-pyrazolidone, 4-methyl-4-hydroxymethyl-1-phenyl-3-pyrazolidone and 4-methyl-4-hydroxymethyl-1-p-tolyl-3-pyrazolidone, etc.; and ascorbic acids, etc., which are used alone or in combination. Further, in order to obtain dye images from dye forming couplers, it is possible to use aromatic primary amine developing agents and, preferably, p-phenylenediamine type developing agents. Examples of these include 4-amino-3-methyl-N,N-diethylaniline hydrochloride, N,N-diethyl-p-phenylenediamine, 3-methyl-4-amino-N-ethyl-N-β-(methanesulfonamido)ethylaniline, 3-methyl-4-amino-N-ethyl-N-(β-sulfoethyl)aniline, 3-ethoxy-4-amino-N-ethyl-N-(β-sulfoethyl)aniline and 4-amino-N-ethyl-N-(β-hydroxyethyl)aniline. Such developing agents may be incorporated in alkaline processing compositions (processing elements) or may be incorporated in suitable layers of light-sensitive materials.

In case of using DRR compounds in the present invention, any silver halide developing agent (or electron transfer agent) may be used if it can cause cross-oxidation of the DRR compounds. Particularly, 3-pyrazolidones are preferred.

The developing solution may contain sodium sulfite, potassium sulfite, ascorbic acid, reductones (for example, piperidinohexose ledactone), and the like as preservatives.

The light-sensitive materials of the present invention can be developed with a surface developing solution to directly obtain positive images. The surface developing solution is such a solution that the development step is substantially induced by latent image or fog specks on the surface of silver halide grains. Although it is preferred that the developing solution does not contain solubilizing agents for silver halide, it may contain a small amount of solubilizing agents for silver halide (for example, sulfites) provided that the inner latnet images do not substantially contribute to development until development by the centers of surface development of the silver halide grains is concluded.

The developing solution may contain sodium hydroxide, potassium hydroxide, sodium carbonate, potassium carbonate, sodium tertiary phosphate, sodium metaborate, etc. as alkali agents and buffer agents. The amount of these agents are selected so that the pH of the developing solution is in a range of 10 to 13, preferably 11 to 12.5.

The developing solution may contain color development accelerators such as benzyl alcohol, etc. It is advantageous that the developing solution further contains compounds which are conventionally used as antifogging agents, for example, benzimidazoles such as 5-nitrobenzimidazole and benzotriazoles such as benzotriazole, 5-methyl-benzotriazole, etc. in order to reduce the minimum density of direct positive images.

The light-sensitive materials of the present invention can be processed with a viscous developing solution.

The viscous developing solution is a liquid composition containing processing components necessary to develop silver halide emulsions and to form diffusion transfer dye images, which contains water as a main solvent and may contain other hydrophilic solvents such as methanol or methyl cellosolve. The processing composition contains alkalis in an amount necessary to maintain a pH for development of emulsion layers and to neutralize acids formed during processes of development and dye image formation (for example, hydrohalogenic acids such as hydrobromic acid and carboxylic acids such as acetic acid, etc.). As alkalis used, there are alkali metal salts, alkaline earth metal salts and amines such as lithium hydroxide, sodium hydroxide, potassium hydroxide, calcium hydroxide dispersion, tetramethyl ammonium hydroxide, sodium carbonate, sodium tertiary phosphate, diethylamine, etc. It is preferred to incorporate caustic alkali in such an amount that the pH becomes about 12 or more (particularly, 14 or more). More preferably, the processing composition contains hydrophilic polymers having a high molecular weight such as polyvinyl alcohol, hydroxyethyl cellulose or sodium carboxymethyl cellulose. These polymers are preferably used in such an amount that the processing composition has a viscosity of 1 poise or more and preferably 500 to 1000 poises at room temperature.

It is particularly advantageous in the case of monosheet film units that the processing composition contains light absorbing substances such as carbon black or pH indicating dyes or desensitizers such as those described in U.S. Pat. No. 3,579,333 for the purpose of preventing fogging of silver halide emulsions by outside light during or after processing. Further, to the processing composition, it is possible to add developing restrainers such as benzotriazole.

The above described processing composition is preferably packaged in rupturable containers described in U.S. Pat. Nos. 2,543,181, 2,643,886, 2,653,732, 2,723,051, 3,056,491, 3,056,492 and 3,152,515, etc.

In the case of using the light-sensitive materials of the present invention for a diffusion transfer photographic process, the light-sensitive materials are preferred to have the form of a film unit. The photographic film unit, namely, the film unit which is processed by passing through a pair of pressing members placed in parallel, is composed fundamentally of the following three elements:

(1) Light-sensitive element containing a nucleating agent of the present invention.
(2) Image receiving element, and
(3) Processing element: The processing element has a means for releasing an alkaline processing composition in the interior of the film unit, such as a rupturable container, and, if necessary, contains a silver halide developer.

A preferred form of this photographic film unit is a type for unifying by superposition, which is disclosed in Belgium Pat. No. 757,959. According to this embodiment, an image receiving layer, a substantially opaque light reflection layer (for example, a TiO₂ layer and a carbon black layer) and a light-sensitive element consisting of one or more silver halide light-sensitive layers combined with DRR compounds are applied in this order to a transparent base, and a transparent cover sheet is placed on the structure so as to have a face-to-face relation. A rupturable container containing an alkaline processing composition containing a clouding agent (for example, carbon black) is placed so as to be adjacent to the top layer of the above described light-sensitive layers and the transparent cover sheet. Such as film unit is exposed to light through the transparent cover sheet. When the film unit is removed from the camera, the container is ruptured by pressing members to spread the processing composition (containing a clouding agent) between the protective layer on the light-sensitive layers and the cover sheet. Thus, the film unit is shielded from light and the development proceeds. The cover sheet is preferred to have a structure that a neutralizing layer and, if desired, a neutralizing rate controlling layer (timing layer) are applied in this order to a base.

Further, other available forms of unification capable of using the DRR compounds or the diffusible dye releasing couplers have been described in U.S. Pat. Nos. 3,415,644, 3,415,645, 3,415,646, 3,647,487 and 3,635,707 and German patent application (OLS) No. 2,426,980, etc.

In the following, examples of the present invention are illustrated. However, the present invention is not to be construed as limited to the Examples.

EXAMPLE 1

To 80 g of a monodispersed inner latent image type direct positive silver halide emulsion (silver amount: 6 to 7 wt%, gelatin: 5 wt%) which was obtained by chemically sensitizing the inner part of grains and the surface of grains with gold and sulfur, respectively, in a process of forming silver halide crystals by adding silver nitrate and potassium bromide at the same time, Compounds 1 and 2 as nucleating agents of the present invention or Comparative Compound A as a known nucleating agent were added in a state of solution in methanol or solution in water-methanol mixture, in an amount of $10^{-10}$ mols to $10^{-8}$ mols per gram of the emulsion, respectively. To the emulsion, gelatin and other conventional additives for emulsions (hardeners or coating aids, etc.) were added. The resulting emulsion was applied to a transparent cellulose triacetate film and dried (silver amount: 4.3 g/m², gelatin: 7.1 g/m²). After this film was subjected to wedge exposure by a tungsten light source at 400 luxes for 1/100 seconds, it was developed for 8 minutes with a surface developing solution having the composition described below. Further, development silver densities obtained by varying the development time from 0 to 8 minutes using the same developing solution were measured, and the development progress rate of the emulsion was determined.

Comparative Compound A

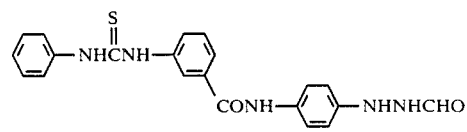

(Surface developing solution)

| | |
|---|---|
| N—Methyl-p-aminophenol sulfate | 2.5 g |

Comparative Compound A

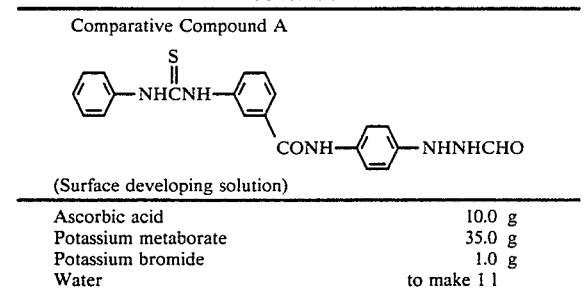

(Surface developing solution)

| Ascorbic acid | 10.0 g |
|---|---|
| Potassium metaborate | 35.0 g |
| Potassium bromide | 1.0 g |
| Water | to make 1 l |

In Table 1, the relation between amount of the nucleating agents and maximum density (D max) of development silver is shown. It is clear from the results shown in the table that exemplified compounds of the present invention give sufficient D max in a very low level of addition as compared with the comparative compound, and the saturation value of D max of the compounds of the present invention is essentially higher than that of the comparative compound.

Then, in order to compare the development rate, the time required to give D max of 0.5 from initiation of the development was measured at 10° C. and 25° C. The results are shown in Table 2. It is seen that the compounds of the present invention are excellent in the effect of accelerating development progress at any temperature.

TABLE 1

| Amount Added ($\times 10^{-8}$ mols/g emulsion) | D max | | |
|---|---|---|---|
| | Exemplified Compound | | Comparative Compound A |
| | 1 | 2 | |
| 0.02 | 0.8 | 0.8 | 0 |
| 0.05 | 0.94 | 0.94 | 0 |
| 0.10 | 0.99 | 0.97 | 0 |
| 0.20 | 1.02 | 1.00 | 0.3 |
| 0.50 | 1.05 | 1.02 | 0.9 |
| 0.80 | 1.07 | 1.04 | 0.95 |
| 1.00 | 1.07 | 1.05 | 0.95 |

TABLE 2

| Nucleating Agent | Time required to reach D max = 0.5 | |
|---|---|---|
| | 25° C. | 10° C. |
| Exemplified Compound 1 | 66 | 144 |
| Exemplified Compound 2 | 84 | 156 |
| Comparative Compound A | 96 | 174 |

EXAMPLE 2

Four color direct positive sensitive sheets (A) to (D) were produced by applying each layer to a polyethylene terephthalate transparent base in the following order.

(1) A mordant layer containing the following copolymer (3.0 g/m$^2$) and gelatin (3.0 g/m$^2$).

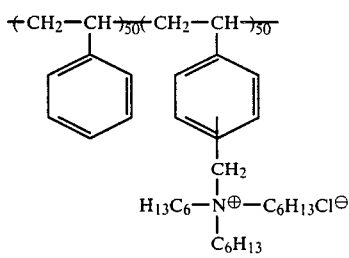

(2) A white reflection layer containing titanium oxide (18 g/m$^2$) and gelatin (2.0 g/m$^2$).

(3) A light shielding layer containing carbon black (1.0 g/m$^2$) and gelatin (1.0 g/m$^2$).

(4) A layer containing the magenta DRR compound represented by the following structural formula I (0.21 g/m$^2$), the DRR compound represented by the following structural formula II (0.11 g/m$^2$), tricyclohexyl phosphate (0.08 g/m$^2$), 2,5-di-tert-pentadecylhydroquinone (0.009 g/m$^2$) and gelatine (0.9 g/m$^2$).

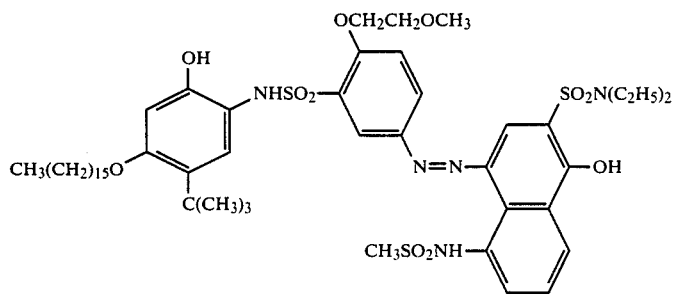

Structural formula I

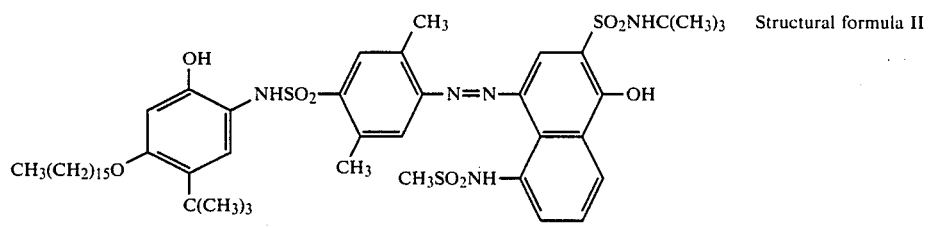

Structural formula II (5) A green-sensitive emulsion layer containing an inner latent image type direct positive silver bromide emulsion sensitized with dyes (silver amount: 0.82 g/m$^2$), gelatine (0.9 g/m$^2$), 2-sulfo-5-n-pentadecylhydroquinone sodium salt (0.08 g/m²) and the following nucleating agent ($10^{-10}$ mols to $10^{-9}$ mols per gram of emulsion).

| Light sensitive sheet | (A) | Compound 1 |
| " | (B) | Compound 2 |
| " | (C) | Comparative Compound A used in Example 1 |
| " | (D) | The following Comparative Compound B described in U.S. Pat. Nos. 3,227,552 and 4,080,207. |

Comparative Compound B

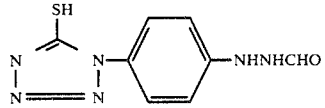

(6) A protective layer containing gelatine (1.0 g/m²).

The above described light-sensitive sheets (A) to (D) were combined with the following processing element and cover sheet and subjected to exposure and development processing.

| Processing Element (Processing solution) | |
|---|---|
| 1-Phenyl-4-methyl-4-hydroxymethyl-3-pyrazolidone | 8.0 g |
| Tert-butylhydroquinone | 0.1 g |
| 5-Methylbenzotriazole | 2.5 g |
| Benzyl alcohol | 1.5 ml |
| Sodium sulfite (anhydrous) | 1.5 g |
| Carboxymethyl cellulose Na salt | 61 g |
| Zinc nitrate 6 hydrate | 0.4 g |
| Carbon black | 410 g |
| Potassium hydroxide | 56 g |
| H₂O | 260 ml |

"Containers capable of breaking by pressure", in rupturable containers, were filled with 0.8 g of the processing solution having the above described composition.

Cover Sheet

A cover sheet was produced by applying polyacrylic acid (10 wt% aqueous solution having a viscosity of about 1000 cp) (15 g/m²) to a polyethylene terephthalate base to form and acid polymer layer (neutralizing layer) and applying acetyl cellulose (3.8 g/m²) and styrene-maleic anhydride copolymer (composition (molar ratio) styrene: maleic anhydride = about 60:40, molecular weight: about 50,000) (0.2 g/m²) to the above described layer.

Processing Step

The above described cover sheet was put on the above described light-sensitive sheet. After the light-sensitive sheet was subjected to wedge exposure for 1/100 seconds by a tungsten light source through the cover sheet, the above described processing solution was spread between both sheets by press rolls so as to result in a thickness of 100μ. The spread processing was carried out at 25° C. Thereafter, the green density of images formed on the image receiving layer was measured by a Macbeth reflection densitometer through the transparent base of the light-sensitive sheet, after the passage of 1 hour from the processing. Results are shown in Table 4.

As with the results in Example 1, it is understood from Table 3 that the nucleating agents of the present invention are excellent because they give a high density when added in a small amount to the color direct positive emulsion.

TABLE 3

| Amount added ($10^{-9}$ mols/g of emulsion) | D max Light-sensitive sheet | | | |
|---|---|---|---|---|
| | (A) | (B) | Comparison (C) | Comparison (D) |
| 0.3 | 1.6 | 0.7 | 0.05 | 0 |
| 0.4 | 2.1 | 1.3 | 0.1 | 0.05 |
| 0.5 | 2.1 | 1.8 | 0.15 | 0.08 |
| 0.6 | 2.1 | 1.9 | 0.25 | 0.1 |
| 0.8 | 2.1 | 2.0 | 0.6 | 0.22 |
| 1.0 | 2.1 | 2.1 | 1.2 | 0.5 |
| 1.5 | 2.1 | 2.1 | 1.6 | 2.0 |
| 2.0 | 2.1 | 2.1 | 1.6 | 2.1 |

EXAMPLE 3

Color direct positive photographic light-sensitive sheet (D) was produced by applying each layer to a polyethylene terephthalate transparent base in the following order.

(1) The same mordant layer as in Example 2.
(2) The same white reflection layer as in Example 2.
(3) The same light shielding layer as in Example 2.
(4) A layer containing the following cyan DRR compound (0.44 g/m²), tricyclohexyl phosphate (0.09 g/m²), 2,5-di-tert-pentadecylhydroquinone (0.08 g/m²) and gelatine (0.8 g/m²).

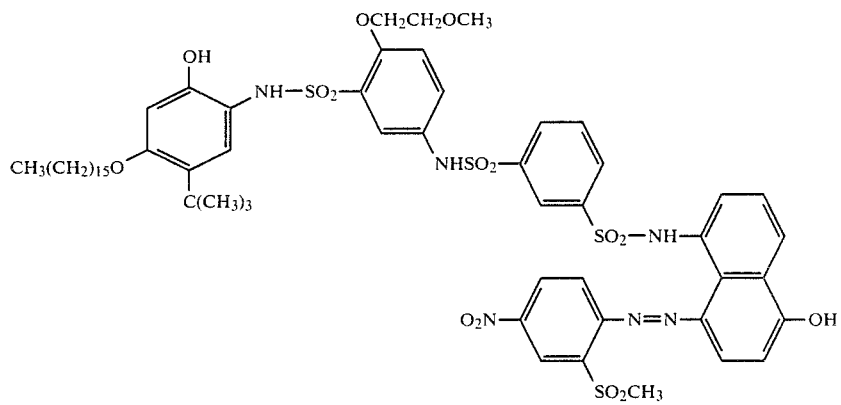

(5) A red-sensitive emulsion layer containing a red-sensitive inner latent image type direct positive silver bromide emulsion sensitized with dyes (silver amount:

1.03 g/m²), gelatine (1.2 g/m²), 2-sulfo-5-n-pentadecylhydroquinone sodium salt (0.13 g/m²) and Compound 1 (0.0039 mg/m²).

(6) A layer containing 2,5-di-tert-pentadecylhydroquinone (0.43 g/m²), trihexyl phosphate (0.1 g/m²) and gelatine (0.4 g/m²).

(7) The same magenta coloring matter layer as the layer (4) as in Example 2.

(8) The same green-sensitive silver bromide emulsion layer as the layer (5) in Example 2, except that it contained 0.00033 mg/m² of Compound 1 as a nucleating agent.

(9) The same layer as in (6).

(10) A layer containing the yellow DRR compound having the following structure (0.53 g/m²), tricyclohexyl phosphate (0.13 g/m²), 2,5-di-tert-pentadecylhydroquinone (0.014 g/m²) and gelatine (0.7 g/m²).

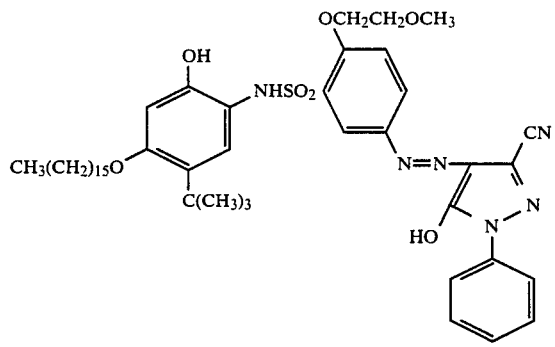

(11) A blue-sensitive emulsion layer containing a blue-sensitive inner latent image type direct positive silver bromide emulsion sensitized with dyes (silver amount: 1.09 g/m²), gelatine (1.1 g/m²), 2-sulfo-5-n-pentadecylhydroquinone sodium salt (0.07 g/m²) and Compound 1 (0.0013 mg/m²).

(12) A protective layer containing gelatine (1.0 g/m²).

After the above described light-sensitive sheet was subjected to wedge exposure through a color test chart, development was carried out with the same processing solution and cover sheet as in Example 2 at 10° C., 25° C. or 35° C. Color densities of yellow, magenta and cyan in the formed images were measured after passage of 1 hour from spread processing.

Further, light-sensitive sheet (E) which contained Comparative Compound A as a nucleating agent in the layers (5), (8) and (11) in the following amounts instead of Compound 1 was produced.

| Layer (5) | Comparative Compound A | 0.020 mg/m² |
| Layer (8) | " | 0.0030 mg/m² |
| Layer (11) | " | 0.013 mg/mm² |

Maximum densities of yellow (Y), magenta (M) and cyan (C) obtained at processing temperatures of 10° C., 25° C. and 35° C. are shown in Table 4. It is obvious that, in the light-sensitive sheet (D) using the nucleating agent of the present invention, dependence of maximum density on processing temperature is small as compared with the case of the light-sensitive sheet (E) using the prior nucleating agent, and reduction of density at a low temperature (10° C.) is prevented in each layer to improve photographic properties.

TABLE 4

| Processing | D max | | | | | |
| | Sheet (D) | | | Sheet (E) | | |
| temperature | Y | M | C | Y | M | C |
| --- | --- | --- | --- | --- | --- | --- |
| 10° C. | 1.65 | 1.30 | 0.90 | 1.60 | 1.05 | 0.45 |
| 25° C. | 1.75 | 2.00 | 1.80 | 1.75 | 1.90 | 0.60 |
| 35° C. | 1.70 | 2.00 | 2.00 | 1.65 | 1.90 | 1.95 |

EXAMPLE 4

A separation type light-sensitive unit was produced as follows. To a polyethylene terephthalate black base to which carbon black was applied, the following layers (1) to (11) were applied in turn to produce light-sensitive sheet (F).

(1) The same cyan coloring material layer as the layer (4) in Example 3.

(2) The same red-sensitive direct positive silver bromide emulsion layer as the layer (5) in Example 3.

(3) An intermediate layer containing 2,5-di-(tertpentadecyl)hydroquinone (0.71 g/m²), vinylpyrrolidonevinyl acetate copolymer (molar ratio 7:3) (0.24 g/m²) and gelatine (0.6 g/m²).

(4) A layer containing gelatine (0.4 g/m²).

(5) The same magenta coloring matter layer as the layer in Example 3.

(6) The same green-sensitive direct positive silver bromide emulsion layer as the layer (8) in Example 3.

(7) The same layer as in (3).

(8) The same layer as in (4).

(9) The same yellow coloring matter layer as the layer (10) in Example 3.

(10) The same blue-sensitive direct positive silver bromide emulsion layer as the layer (11) in Example 3.

(11) A protective layer containing gelatine (1 g/m²).

Further, light-sensitive sheet (G) which contained Comparative Compound A in the emulsion layers (2), (6) and (10) in the following amounts instead of Compound 1 was produced.

| Layer (2) | Comparative Compound A | 0.020 mg/m² |
| Layer (6) | " | 0.0030 mg/m² |
| Layer (10) | " | 0.013 mg/m² |

A dye image receiving sheet was produced by applying the following layers (12)-(16) in turn to a polyester white base in which a carbon black layer and a titanium oxide layer were applied to the back in turn.

(12) A layer containing acrylic acid-butyl acrylate copolymer having a ratio by weight of 80:20 (22 g/m²) and 1,4-bis-(2,3-epoxypropoxy)butane (0.44 g/m²).

(13) A layer containing acetyl cellulose (3.8 g/m²), styrene-maleic acid anhydride copolymer having a ratio by weight of 60:40 (0.2 g/m²) and 5-(β-cyanoethylthio)-1-phenyltetrazole (0.115 g/m²).

(14) A layer containing a latex of vinylidene chloride-methyl acrylate-acrylic acid terpolymer having a ratio by weight of 85:12:3 (2.5 g/m²) and a polymethyl methacrylate latex (0.05 g/m²).

(15) The same mordant layer as the layer (1) in Example 2.

(16) A layer containing phthalated gelatine (1 g/m²).

After the above described light-sensitive sheet was subjected to wedge exposure through a color test chart, the above described image receiving sheet was put on the light-sensitive sheet and a processing solution having the following composition put in a container was spread by pressure rolls so as to result in a thickness of 60 μm. After the passage of 1 minute, both sheets were separated.

| (Processing solution) | |
| --- | --- |
| 1-(p-Tolyl)-4-hydroxymethyl-4-methyl-3-pyrazolidone | 0.4 g |
| Methylhydroquinone | 0.012 g |
| 5-Methylbenzotriazole | 0.7 g |
| Benzyl alcohol | 0.3 ml |
| Sodium sulfite (anhydrous) | 0.18 g |
| Hydroxymethyl cellulose | 4.0 g |
| Potassium hydroxide | 6.3 g |
| H$_2$O | 67 ml |

It is understood from Table 5 that the mercapto nucleating agent of the present invention gives excellent photographic properties in a sufficiently small amount as compared with the comparative nucleating agent.

TABLE 5

| | Light-sensitive sheet (F) | Light-sensitive sheet (G) |
| --- | --- | --- |
| D max | | |
| Yellow | 1.86 | 1.82 |
| Magenta | 2.01 | 1.98 |
| Cyan | 2.04 | 2.08 |
| D min | | |
| Yellow | 0.10 | 0.10 |
| Magenta | 0.12 | 0.12 |
| Cyan | 0.17 | 0.18 |

While the invention has been described in detail and with reference to specific embodiment thereof, it will be apparent to one skilled in the art that various changes and modifications can be made therein without departing from the spirit and scope thereof.

What is claimed is:

1. A direct-positive silver halide photographic light-sensitive material comprising a support having thereon at least one inner latent image light-sensitive silver halide photographic emulsion layer, and containing in said photographic emulsion layer or at least one of other hydrophilic colloid layers a mercapto compound represented by the following general formula (I) or (II) as a nucleating agent:

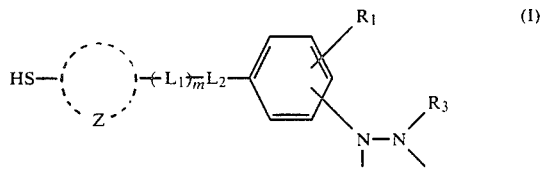

(I)

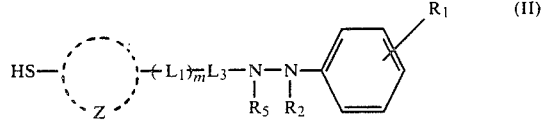

(II)

wherein Z represents an atomic group necessary to form a mononuclear or condensed nitrogen-containing heterocyclic ring, L$_1$ represents a divalent organic group, m represents 0 or 1, L$_2$ represents —CONR—, —NRCO—, —SO$_2$NR—, —NRSO$_2$—, —OCO—, —COO—, —S—, —NR—, —CO—, —SO—, —SO$_2$—, —OCOO—, —NRCONR'—, —NRCOO—, —OCONR— or —NRSO$_2$NR'—, wherein R and R' each represents a hydrogen atom, an alkyl group or an aryl group, L$_3$ represents —CO—, —SO— or —SO$_2$—, R$_1$ represents a hydrogen atom, an alkyl group, a halogen atom, an alkoxy group, a carbonamide group or a sulfonamide group, R$_2$ represents a hydrogen atom or an alkoxycarbonyl group, R$_3$ represents an acyl group, an alkylsulfonyl group, an arylsulfonyl group, an alkylsulfinyl group, an arylsulfinyl group, an alkoxycarbonyl group, an aryloxycarbonyl group, a carbamoyl group, a sulfamoyl group or a sulfinamoyl group, R$_4$ represents a hydrogen atom, and R$_3$ may form the partial structure:

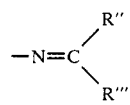

of hydrazone together with R$_4$ and a nitrogen atom, and R$_5$ represents a hydrogen atom or forms the partial structure: —C=N— of hydrazone together with L$_3$ and a nitrogen atom, wherein one of two bonds of the carbon atom in

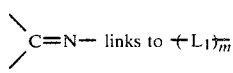

and the other of two bonds of the carbon atom links to R'', R'' represents an alkyl group, an aryl group or a heterocyclic group, and R''' represents a hydrogen atom, an alkyl group, an aryl group or a heterocyclic group.

2. The direct-positive silver halide photographic light-sensitive material according to claim 1, wherein the nitrogen-containing heterocyclic ring formed by Z is pyrrole, pyrazole, imidazole, triazole, tetrazole, pyridine, pyrimidine, pyrazine, pyridazine, triazine, imidazole, benzimidazol or azaindene.

3. The direct-positive silver halide photographic light-sensitive material according to claim 1, wherein the divalent organic group represented by L$_1$ is selected from a divalent group consisting of alkylene, alkenylene, phenylene, —O—, —S—, —CO—, —SO—, —SO$_2$— and imido, alone or in combination.

4. The direct-positive silver halide photographic light-sensitive material according to claim 1, wherein the compound represented by the general formula (I) and (II) is a compound represented by the following general formula (III):

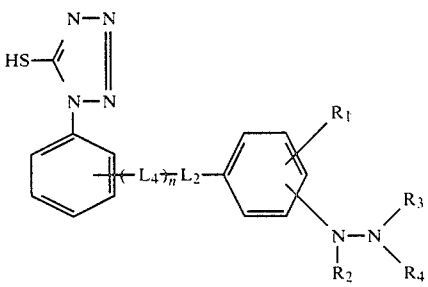

wherein $L_2$, $R_1$, $R_2$, $R_3$ and $R_4$ have the same meaning as in the general formula (I), or represents 0 or 1, and $L_4$ is selected from $L_1$ in the general formula (I).

5. The direct-positive silver halide photographic light-sensitive material according to claim 1, wherein the compound represented by the general formula (I) and (II) is Compound 1,

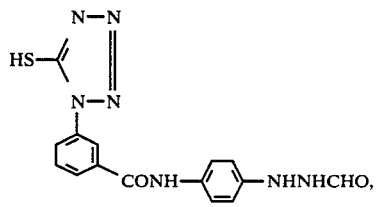

Compound 1

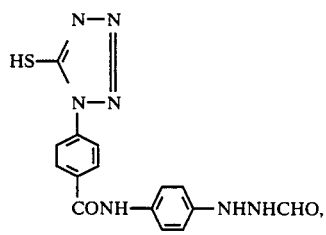

Compound 2

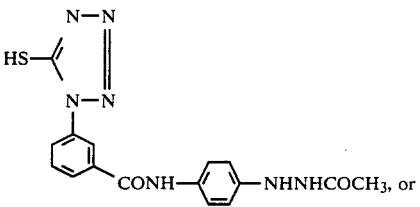

Compound 3

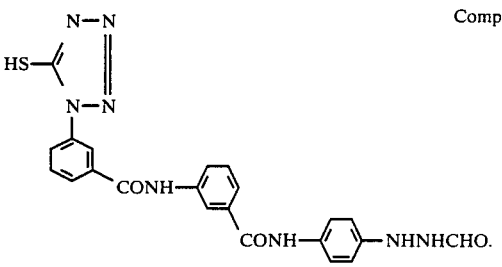

Compound 13

6. The direct-positive silver halide photographic light-sensitive material according to claim 1, wherein the light-sensitive silver halide photographic emulsion layer is associated with a diffusible dye-releasing dye image providing compound having a N-substituted sulfamoyl group.

7. The direct positive silver halide photographic light-sensitive material according to claim 1, wherein said light-sensitive material is a film unit for a diffusion transfer process, into which a rupturable container having a processing solution is incorporated.

8. A photographic light-sensitive material according to claim 7, wherein a compound represented by the general formula (I) or (II) is contained in said processing solution.

9. A photographic light-sensitive material according to claim 1, wherein the inner latent image silver halide emulsion comprises silver bromide, silver iodobromide or silver chloriodobromide with an iodide content of 10 mol % or less and a chloride content of 30 mol % or less.

* * * * *